United States Patent [19]

Wong et al.

[11] Patent Number: 5,075,225
[45] Date of Patent: Dec. 24, 1991

[54] PROCESS FOR THE ENZYMATIC SYNTHESIS OF NUCLEOSIDES

[75] Inventors: Chi-Huey Wong; William J. Hennen, both of College Station, Tex.

[73] Assignee: The Texas A&M University System, College Station, Tex.

[21] Appl. No.: 334,699

[22] Filed: Apr. 6, 1989

[51] Int. Cl.$^5$ .................. C12P 19/38; C12P 19/40; C12P 19/30; C12N 9/12
[52] U.S. Cl. ............................ 435/87; 435/88; 435/89; 435/194
[58] Field of Search .............. 435/87, 88, 194, 89

[56] References Cited

U.S. PATENT DOCUMENTS

| | | | |
|---|---|---|---|
| 4,347,315 | 8/1982 | Krenitsky et al. | 435/87 |
| 4,381,344 | 4/1983 | Rideout et al. | 435/87 |
| 4,594,320 | 6/1986 | Fujishima | 435/89 |
| 4,594,321 | 6/1986 | Fujishima | 435/88 |

OTHER PUBLICATIONS

Krenitsky, et al., J. Med. Chem., 1986, vol. 29, pp. 138-143.
Krenitsky, et al., Carbohydrate Research, 1981, vol. 97, pp. 139-146.
Krenitsky et al., Biochemistry, 1981, vol. 20, pp. 3615-3621.
Krenitsky, et al., J. Med. Chem., 1982, vol. 25, pp. 32-35.
Rideout, et al., J. Med. Chem., 1982, vol. 25, pp. 1040-1044.
Utagawa, et al., Agric. Biol. Chem., 1986, vol. 50(1), pp. 121-126.
Jones, et al., J. Am. Chem., 1963, vol. 85, pp. 193-201.
Kulikowska, et al., Biochem. Biophys. Acta., 1986, vol. 874, pp. 355-363.
Stoeckler, et al., Fed. Proc. Fed. Am. Soc. Exp. Biol., 1986, vol. 45, pp. 2773-2778.
Witkowski et al., J. Med. Chem., 1972, vol. 15 (11), pp. 1150-1154.
Rousseau, et al., Biochemistry, 1966, vol. 5, pp. 756-760.
Stoltzfus, et al., J. Virol., 1981, vol. 38, pp. 173-183.
Oivanen, et al., J. Tet., 1987, vol. 43, pp. 1133-1140.
Ryba, et al., J. Chromatography, 1981, vol. 211, pp. 337-346.
Tener, et al., J. Chem. Soc., 1957, vol. 79, pp. 441-443.
Enzyme Nomenclature, Academic Press, 1984.
Hupe, et al., Ann. Reports in Medicinal Chemistry, Bailey, Ed., Academic Press, New York, 1986, vol. 21, Ch. 23.
Mansuri, et al., Ann. Reports in Medicinal Chemistry, Bailey, Ed., Academic Press, New York, 1987, vol. 22, Ch. 15.
Mansuri, et al., Ann. Reports in Medicinal Chemistry, Allen, Ed., Academic Press, New York, 1988, vol. 23, Ch. 17.
Ezzell, Nature, 1987, vol. 326, p. 430.
DeClerg, Trends in Pharmacol. Sci., 1987, vol. 8, pp. 339-345.
Lerch, Antiviral Res., 1987, vol. 7, pp. 257-270.
Vanek, et al., J. Coll. Czech. Chem. Commun., 1984, vol. 49, pp. 2492-2495.
Sidewall, et al., Science, 1972, vol. 177, pp. 705-706.
Utagawa, et al., Agric. Biol. Chem., 1985, vol. 49, p. 3229.
Nucleoside Analogues; Chemistry, Biology and Medicinal Applications, Walker, et al., Eds., NATO Advanced Study Institutes Seires, Plenum, New York, 1979, vol. 26.
Suhadolnik, Nucleoside Antibiotics, J. Wiley, New York, 1970.
Suhadolnik, Nucleosides as Biological Probes, J. Wiley, New York, 1979.
Robbins, et al., Can. J. Chem., 1973, vol. 51, p. 3161.
Mizuno, et al., Chem. Pharm. Bull., 1964, vol. 12, p. 866.

*Primary Examiner*—Herbert J. Lilling
*Attorney, Agent, or Firm*—Arnold, White & Durkee

[57] ABSTRACT

A process for synthesizing nucleosides is disclosed. The process includes the reaction of an alkylated nucleoside (such as 7-methylguanosine or 7-methylinosine) with a heterocyclic base (such as adenine, 3-deazaadenine or 1,2,4-triazole-3-carboxamide) in the presence of a nucleoside-forming enzyme to form a nucleoside that includes a glycosyl component, donate by the alkylated nucleoside, bonded to the heterocyclic base.

19 Claims, 3 Drawing Sheets

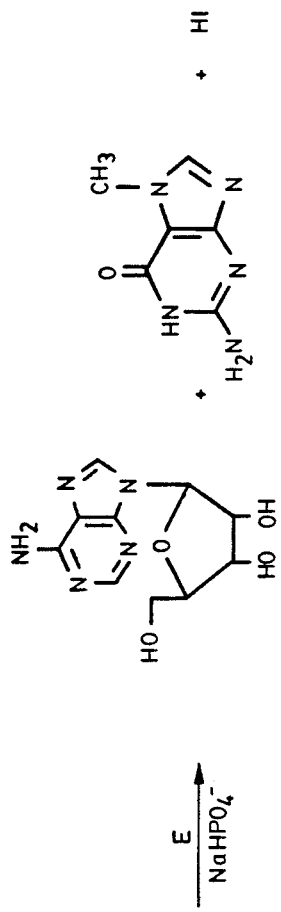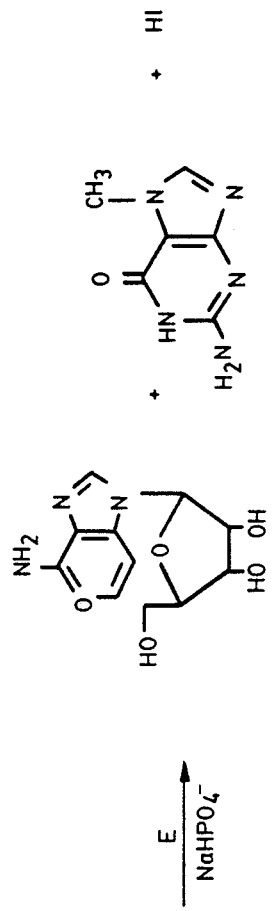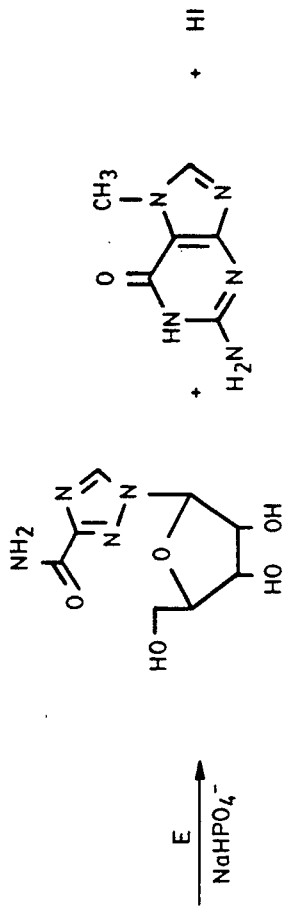
FIG.1  FIG.2  FIG.3
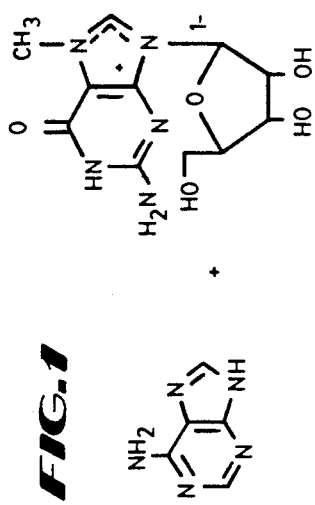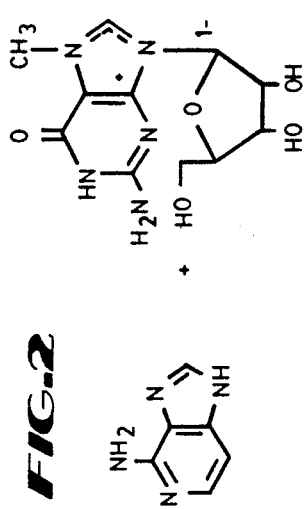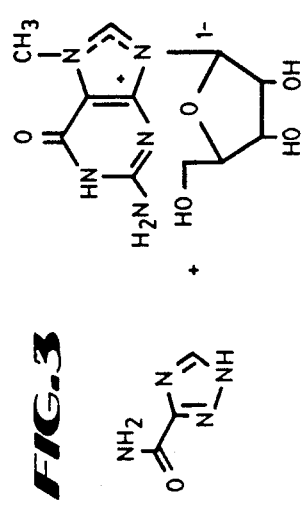

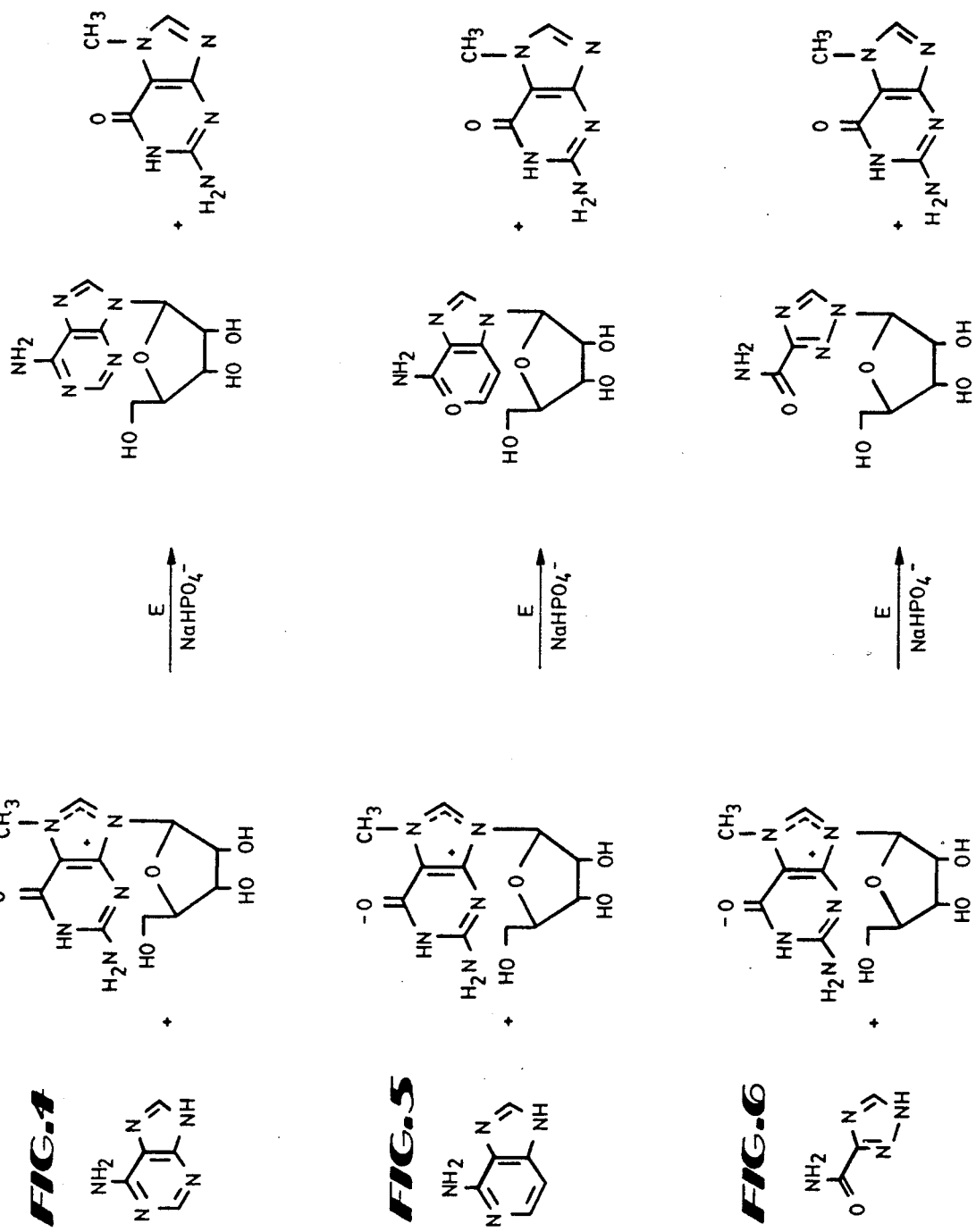

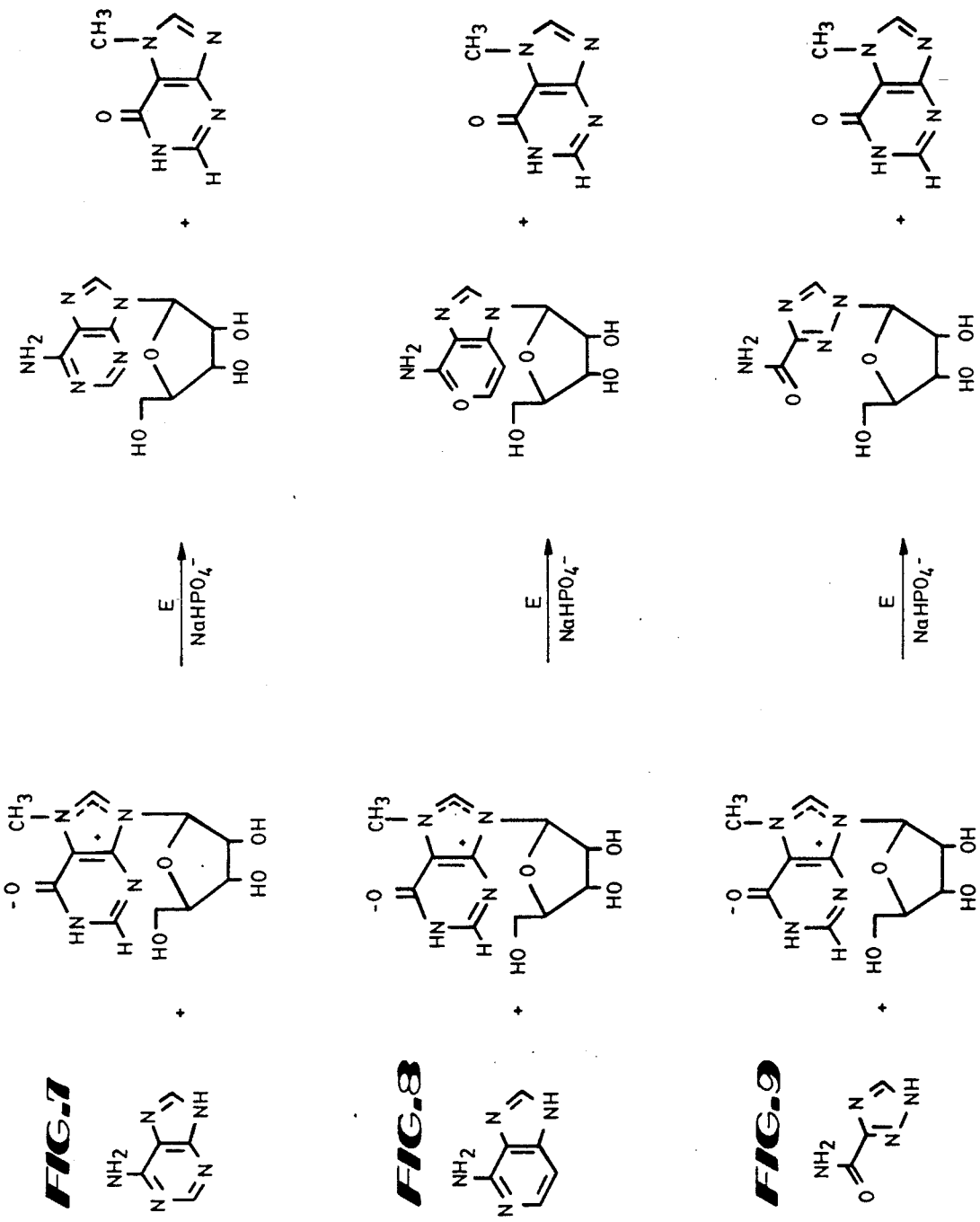

PROCESS FOR THE ENZYMATIC SYNTHESIS OF NUCLEOSIDES

BACKGROUND OF THE INVENTION

The present invention relates to a process for making nucleosides, nucleoside analogs and derivatives. The invention has particular application to the enzymatic synthesis of nucleosides, nucleoside analogs and derivatives.

Nucleoside analogs have been used extensively as antibiotic substances and as biological probes. See Suhadolnik, *Nucleoside Antibiotics*, J. Wiley, New York, 1970; Suhadolnik, *Nucleosides as Biological Probes*, J. Wiley, New York, 1979; *Nucleoside Analogues; Chemistry, Biology and Medicinal Applications*, Walker, et al., Eds., NATO Advanced Study Institutes Series, Plenum, New York, 1979, Vol. 26. Recent interest in this class of compounds has been stimulated by the efficacy of certain nucleosides as anti-parasitic and antiviral agents. See Hupe, *Ann. Reports in Medicinal Chemistry*, Bailey, Ed., Academic Press, New York, 1986, Vol. 21., Ch. 23; Mansuri, et al., *Ann. Reports in Medicinal Chemistry*, Bailey, Ed., Academic Press, New York, 1987, Vol. 22, Ch. 15; Mansuri, et al., *Ann Reports in Medicinal Chemistry*, Allen, Ed., Academic Press, New York, 1988, Vol. 23, Ch. 17. Zidovudine (3'-azido-3'-deoxythymidine, AZT) and the various 2',3'-dideoxynucleosides have received special attention because of their virucidal activity in the treatment of AIDS patients See Ezzell, *Nature*, 1987, Vol. 326, p. 430; DeClerq, *Trends in Pharmacol. Sci.*, 1987, Vol. 8, pp. 339–45. The broad-spectrum antiviral activity of 1-($\beta$-D-ribofuranosyl)-1,2,4-triazole-3-carboxamide (hereinafter referred to as RTCA) has recently been shown to extend to the treatment of plant as well as animal viruses. See Lerch, *Antiviral Res.*, 1987, Vol. 7, pp. 257–70.

Traditionally, nucleosides have been prepared by various chemical methods, including those described in *Nucleoside Analogues; Chemistry, Biology and Medicinal Applications*, Walker, et al., Eds., NATO Advanced Study Institutes Series, Plenum, New York, 1979, Vol. 26. Recently, however, a number of papers have appeared reporting the enzymatic preparations of both natural and unnatural nucleosides. See, for example, Krenitsky, et al., *J. Med. Chem.*, 1986, Vol. 29, pp. 138–143; Utagawa, et al., *Agric. Biol. Chem.*, 1986, Vol. 50(1), pp. 121–126; Krenitsky, et al., *Carbohydrate Research*, 1981, Vol. 97, pp. 139–146, Krenitsky, et al., *Biochemistry*, 1981, Vol. 20, pp. 3615–3621.. Many of those papers report transglycosylation reactions wherein the original heterocyclic base is exchanged for a new aglycon moiety. Those works employed two basic strategies.

The first strategy involved the enzymatic preparation of ribose-1-phosphate ("R-1-P") from a nucleoside, followed by the isolation of the R-1-P. The isolated R-1-P was then used as the glycosyl donor in an enzymatic coupling reaction with added heterocycles. An overall purine to purine analog exchange could be accomplished by this means.

The second strategy used a pyrimidine nucleoside as the glycosyl donor and a purine or purine analog as the glycosyl acceptor. This was conducted as a one-pot reaction without the isolation of R-1-P but required that both a pyrimidine nucleoside phosphorylase and purine nucleoside phosphorylase be present in the reaction media.

Of interest here is the report by Utagawa, et al., *Agric. Biol. Chem.*, 1986, Vol. 50(1), pp. 121–126, that the purine analog 1,2,4-triazole-3-carboxamide ("TCA", the aglycon component of RTCA) could not be glycosylated to any measurable extent in a one-pot reaction using inosine as the glycosyl donor and purine nucleoside phosphorylase ("PNPase") as the catalyst. Those workers cited the low affinity of TCA ($K_m = 167$ mM) compared to the affinity of hypoxanthine (the phosphorolysis product of inosine, $K_m = 5.6$ mM) for PNPase. Hypoxanthine perhaps acts as a competitive inhibitor of RTCA synthesis.

The disadvantages of the previous enzymatic strategies are that they require either the isolation of R-1-P or the presence of both pyrimidine and purine nucleoside phosphorylases. There is a need for a new synthetic method that overcomes those restrictions. The process of the present invention provides such a method.

SUMMARY OF THE INVENTION

The present invention provides a process for synthesizing nucleosides, which comprises:

(a) reacting in solution and in the presence of a nucleoside-forming enzyme (i) a first nucleoside comprising an activated heterocyclic base bonded to a glycosyl component with (ii) an unactivated heterocyclic base, the activated heterocyclic base, when dissociated from the glycosyl component of the first nucleoside, providing a relatively poor substrate for the nucleoside-forming enzyme as compared to the unactivated heterocyclic base, for a time sufficient to enable the first nucleoside to donate the glycosyl component for bonding with the unactivated heterocyclic base;

(b) yielding a mixture that includes (i) a second nucleoside comprising the unactivated heterocyclic base bonded to the glycosyl component and (ii) the activated heterocyclic base that has been dissociated from the glycosyl component, and (c) isolating the resulting second nucleoside from the mixture.

BRIEF DESCRIPTION OF THE DRAWINGS

FIG. 1 is a schematic of an embodiment of the process of the present invention wherein the reactants include a first nucleoside (7-methylguanosine.hydroiodide) and an unactivated heterocyclic base (adenine) which react in the presence of an ezyme E (purine nucleoside phosphorylase) and an effective amount of sodium hydrogen phosphate to produce adenosine and 7-methylguanine.

FIG. 2 is a schematic of an embodiment of the process of the present invention wherein the reactants include a first nucleoside (7-methylguanoisine.hydroiodide) and an unactivated heterocyclic base (3-deazaadenine) which react in the presence of an enzyme E (purine nucleoside phosphorylase) and an effective amount of sodium hydrogen phosphate to produce 3-deazaadenosine and 7-methylguanine.

FIG. 3 is a schematic of an embodiment of the process of the present invention wherein the reactants include a first nucleoside (7-methylguanoisine.hydroiodide) and an unactivated heterocyclic base (TCA) which react in the presence of an enzyme E (purine nucleoside phosphorylase) and an effective amount of sodium hydrogen phosphate to produce RTCA and 7-methylguanine.

FIG. 4 is a schematic of an embodiment of the process of the present invention wherein the reactants include a first nucleoside (7-methylguanosine) and an unactivated heterocyclic base (adenine) which react in the presence of an enzyme E (purine nucleoside phosphorylase) and an effective amount of sodium hydrogen phosphate to produce adenosine and 7-methylguanine.

FIG. 5 is a schematic of an embodiment of the process of the present invention wherein the reactants include a first nucleoside (7-methylguanosine) and an unactivated heterocyclic base (3-deazaadenine) which react in the presence of an enzyme E (purine nucleoside phosphorylase) and an effective amount of sodium hydrogen phosphate to produce 3-deazaadenosine and 7-methylguanine.

FIG. 6 is a schematic of an embodiment of the process of the present invention wherein the reactants include a first nucleoside (7-methylguanosine) and an unactivated heterocyclic base (TCA) which react in the presence of an enzyme E (purine nucleoside phosphorylase) and an effective amount of sodium hydrogen phosphate to produce RTCA and 7-methylguanine.

FIG. 7 is a schematic of an embodiment of the process of the present invention wherein the reactants include a first nucleoside (7-methylinosine) and an unactivated heterocyclic base (adenine) which react in the presence of an enzyme E (purine nucleoside phosphorylase) and an effective amount of sodium hydrogen phosphate to produce adenosine and 7-methylhypoxanthine.

FIG. 8 is a schematic of an embodiment of the process of the present invention wherein the reactants include a first nucleoside (7-methylinosine) and an unactivated heterocyclic base (3-deazaadenine) which react in the presence of an enzyme E (purine nucleoside phosphorylase) and an effective amount of sodium hydrogen phosphate to produce 3-deazaadenosine and 7-methylhypoxanthine.

FIG. 9 is a schematic of an embodiment of the process of the present invention wherein the reactants include a first nucleoside (7-methylinosine) and an unactivated heterocyclic base (TCA) which react in the presence of an enzyme E (purine nucleoside phosphorylase) and an effective amount of sodium hydrogen phosphate to produce RTCA and 7-methylhypoxanthine.

DETAILED DESCRIPTION OF SPECIFIC EMBODIMENTS

This invention is a novel process for the enzymatic synthesis of nucleosides, nucleoside analogs and derivatives (hereinafter referred to for simplicity as nucleosides). In the process of the present invention, a first nucleoside is selected which is comprised of a glycosyl component bonded to an activated heterocyclic base. An activated heterocyclic base is a heterocyclic base which, when dissociated from the glycosyl component of the first nucleoside, provides a poor substrate for a nucleoside-forming enzyme, as compared to an unactivated heterocyclic base.

This first nucleoside is reacted with an unactivated heterocyclic base in the presence of a nucleoside-forming enzyme. Nucleoside-forming enzymes include enzymes that either break the bond between the activated heterocyclic base and the glycosyl component, or form the bond between the unactivated heterocyclic base and the glycosyl component, or both. During that reaction, the first nucleoside donates the glycosyl component to the unactivated heterocyclic base, yielding a second nucleoside (which comprises the unactivated heterocyclic base bonded to the glycosyl component) and the activated heterocyclic base that has been dissociated from the glycosyl component. The resulting second nucleoside can then be isolated from the reaction mixture. The process described herein should be generally applicable to the enzymatic glycosylation of unactivated heterocyclic bases.

Because the activated heterocyclic base provides a poor substrate for the nucleoside-forming enzyme when compared to the unactivated heterocyclic base, the unactivated heterocyclic base reacts with the glycosyl component at a faster rate than the activated heterocyclic base reacts with the glycosyl component. Preferably, the difference in the rate at which the unactivated heterocyclic base reacts with the glycosyl component and the rate at which the activated heterocyclic base reacts with the glycosyl component is such that the reaction is essentially irreversible. Such an essentially irreversible process may occur if the activated heterocyclic base undergoes an isomerization, when it is dissociated from the glycosyl component, that renders the activated heterocyclic base a particularly poor substrate for the nucleoside-forming enzyme, i.e., a substrate that in the presence of a nucleoside-forming enzyme reacts with the glycosyl component at a relatively slow rate—if at all. As a result, in mixtures that include equivalent amounts of the first nucleoside and the unactivated heterocyclic base, reacting the first nucleoside with the unactivated heterocyclic base in the presence of a nucleoside-forming enzyme produces at equilibrium a mixture in which there is a substantially greater amount of the second nucleoside (which comprises the unactivated heterocyclic base bonded to the glycosyl component) than the first nucleoside (which comprises the activated heterocyclic base bonded to the glycosyl component).

The activated heterocyclic base of the first nucleoside may be a purine, purine analog or derivative, or a pyrimidine, pyrimidine analog or derivative, that has been modified such that it provides a poor substrate for a nucleoside-forming enzyme, when compared to a heterocyclic base that has not been so modified. The activated heterocyclic base may, for example, be a modified adenine, guanine, hypoxanthine, cytosine, uracil, or thymine.

The activated heterocyclic base used in this process may be similar to the unactivated heterocyclic base used in the process, except for a modification that renders the activated heterocyclic base an inferior substrate for the nucleoside-forming enzyme. For example, the activated heterocyclic base may be a modified guanine, and the unactivated heterocyclic base may be guanine.

Alternatively, the activated heterocyclic base may be very different structurally from the unactivated heterocyclic base. For example, the activated heterocyclic base may be a modified purine, purine analog or derivative and the unactivated heterocyclic base may be a pyrimidine, pyrimidine analog or derivative. (In such a process in which both pyrimidine and purine type heterocyclic bases are mixed together, the reaction mixture must include enzymes (or an enzyme) that can break and form bonds between the glycosyl component and each of the pyrimidine and purine type bases).

The glycosyl component may be a ribose, a ribose analog or derivative, or a deoxyribose, a deoxyribose analog or derivative. The ribose derivative may be, for example, a ribose-5-phosphate. The deoxyribose derivative may be, for example, a deoxyribose-5-phosphate.

The first nucleoside of the present invention may thus be adenosine, guanosine, inosine, uridine, cytidine, thymidine, deoxyadenosine, deoxyguanosine, deoxyinosine, deoxythymidine, deoxyuridine, or deoxycytidine, in which the heterocyclic base has been modified such that, when dissociated from the glycosyl component of the first nucleoside, it provides a relatively poor substrate for the nucleoside-forming enzyme, as compared to an unactivated or unmodified heterocyclic base. Similarly, the first nucleoside of the present invention may be a nucleoside-5-phosphate, i.e., a nucleotide, such as adenosine-5-phosphate, guanosine-5-phosphate, inosine-5-phosphate, thymidine-5-phosphate, uridine-5-phosphate, cytidine-5-phosphate, deoxyadenosine-5-phosphate, deoxyguanosine-5-phosphate, deoxyinosine-5-phosphate, deoxythymidine-5-phosphate, deoxyuridine-5-phosphate, or deoxycytidine-5-phosphate, in which the heterocyclic base has been modified such that, when dissociated from the glycosyl component of the first nucleoside, it provides a relatively poor substrate for the nucleoside-forming enzyme, as compared to an unactivated or unmodified heterocyclic base.

In a preferred embodiment of the present invention, the first nucleoside may be an alkylated nucleoside in which the activated heterocyclic base is a heterocyclic base that has been modified with an alkyl, alkylphenyl, hydroxy alkyl, or hydroxy alkylphenyl substituent. Such a first nucleoside may be made following the procedure described in Jones, et al., *J. Am. Chem.*, 1963, Vol. 85, pp. 193-201. Particularly preferred alkylated nucleosides are the methyl nucleosides, including 7-methylguanosine and 7-methylinosine. Both 7-methylguanosine and 7-methylinosine are substrates for purine nucleoside phosphorylase ("PNPase"), as shown in Kulikowska, et al., *Biochem. Biophys. Acta.*, 1986, Vol. 874, pp. 355-363. PNPase is thus the preferred nucleoside-forming enzyme used in the process of the present invention when 7-methylguanosine or 7-methylinosine are used as the first nucleoside. Because 7-methylguanosine has a $V_{max}=3.3$ $\mu$mol/min per unit of PNPase and a $K_m=14.7$ $\mu$M, it is particularly useful in the process of the present invention. Kulikowska, et al. also report that, at concentrations up to its solubility limit, the activated heterocyclic base of 7-methylguanosine, i.e., 7-methylguanine, does not show product inhibition of the enzyme. Such alkylated nucleosides include heterocyclic bases that have been modified by attachment of an alkyl group to the heterocyclic base so that the alkylated heterocyclic base, when dissociated from the glycosyl component of the alkylated nucleoside, provides a relatively poor substrate for the nucleoside-forming enzyme, as compared to an unalkylated, and therefore unactivated, heterocyclic base.

Nucleoside-forming enzymes other than PNPase may be used in the process of the present invention. As that term is employed herein, nucleoside-forming enzyme refers to any enzyme capable of forming or breaking the C—N bond between the activated or unactivated heterocyclic base component and the glycosyl component of the first and second nucleosides, irrespective of the presence or absence of phosphate. The term is thus not intended to be restricted to only the nucleoside-forming enzymes which require the presence of phosphate to be functional. The nucleoside-forming enzymes that may be used in the process of the present invention include purine nucleoside phosphorylase, pyrimidine nucleoside phosphorylase, uridine phosphorylase, thymidine phosphorylase, nucleoside ribosyltransferase, nucleoside deoxyribosyltransferase, adenine phosphoribosyltransferase, hypoxanthine phosphoribosyltransferase, uracil phosphoribosyltransferase, guanosine phosphorylase, and 5-methylthioadenosine phosphorylase.

The appropriate amount of the nucleoside-forming enzyme to be added to the reaction mixture for different first nucleoside and heterocyclic base reactants will be apparent to those skilled in the art. When a nucleoside phosphorylase enzyme is used as the nucleoside-forming enzyme in the process of the present invention, an effective amount of phosphate must be included in the reaction mixture. In such an embodiment of the process of the present invention, the initial ratio of phosphate to the first nucleoside preferably is between about 0.25 and about 1.0. Variation within that ratio should not noticeably affect the yield of the second nucleoside.

The unactivated heterocyclic base of the present invention may be a purine, purine analog or derivative, or a pyrimidine, pyrimidine analog or derivative. If the activated heterocyclic base is a modified purine, purine analog or derivative, and the unactivated heterocyclic base is an unmodified pyrimidine, pyrimidine analog or derivative, then the reaction mixture must include enzymes (or an enzyme) that can break and form bonds between the glycosyl component and each of the modified purine and the unmodified pyrimidine. Such an enzyme mixture may include a purine nucleoside phosphorylase combined with a pyrimidine nucleoside phosphorylase. Similarly, if a modified pyrimidine, pyrimidine analog, or derivative is used as the activated heterocyclic base and an unmodified purine, purine analog, or derivative purine is used as the unactivated heterocyclic base, then the reaction mixture must include enzymes (or an enzyme) that can break and form bonds between the glycosyl component and each of the modified pyrimidine and the unmodified purine. If the activated heterocyclic base and the unactivated heterocyclic base are both purines, purine analogs or derivatives, or both pyrimidines, pyrimidine analogs or derivatives, then a single nucleoside-forming enzyme may be sufficient to break the bond between the activated heterocyclic base and the glycosyl component of the first nucleoside and to form the bond between the unactivated heterocyclic base and the glycosyl component to form the second nucleoside.

When the first nucleoside of the present invention is a methylguanosine or methylinosine, and the nucleoside-forming enzyme is PNPase, hydrogen ion may be liberated during the reaction. Methylguanosine and methylinosine are both acid labile (meaning that too low a pH will cause cleavage of the glycosidic bond to occur destroying the nucleoside) and base labile (meaning that too high a pH will cause the imidazole ring to open destroying the nucleoside). The enzymatic phosphorolysis of methylguanosine and methylinosine is also strongly pH dependent. Consequently, when those alkylated nucleosides are used as the first nucleoside of the process of the present invention and PNPase is used as the nucleoside-forming enzyme, a weakly buffered (0.1M) phosphate solution corresponding to one mole of phosphate per mole of alkylated nucleoside preferably should be used to maintain the appropriate pH. The solution pH should be monitored and maintained at a pH preferably between about 6.8 and about 8.0, more preferably between about 7.0 and about 7.4, by periodic additions of 0.5N sodium hydroxide.

The following examples are illustrative of the present invention. It will be appreciated, of course, that the proportion of reactants, time of reaction, and temperature of reaction are variable. Selection of different first nucleosides, unactivated heterocyclic bases, and nucleoside-forming enzymes can readily be made. The examples, therefore, are not in any way to be construed as limitations upon the scope of the present invention.

PNPase used in the following examples was obtained from Toyoba Chemical Company. Purine nucleosides were alkylated according to the procedure reported by Jones, et al., *J. Am. Chem.*, 1963, Vol. 85, pp. 193–201, to yield the first nucleosides of the following examples. TCA, of Examples 3, 6, and 9, was synthesized as previously reported by Vanek, et al., *J. Coll. Czech. Chem. Commun.*, 1984, Vol. 49, pp. 2492–2495. 3-deazaadenine, of Examples 2, 5, and 8, was synthesized as previously reported by Krenitsky, et al., *J. Med. Chem.*, 1986, Vol. 29, pp. 138–142. The pH adjustments were made by the addition of 0.5N sodium hydroxide using a pH controller. The reactions were monitored by HPLC on a silica gel 4.6 mm×24 cm column using a mixture of 0.5N ammonium formate (pH 4.2), methanol, and dichloromethane 2:18:80 as the mobile phase, as described by Ryba, et al., *J. Chromatography*, 1981, Vol. 211, pp. 337–346. A UV detector set at 254 nm was used to monitor the column effluent to quantify the consumption of reactants and the formation of products.

EXAMPLE 1

To 10 ml of 0.1M phosphate buffer (pH 7) was added 1.0 mmol of the first nucleoside, 7-methylguanosine.hydroiodide, and 0.25 mmol of the unactivated heterocyclic base, adenine. The solution was adjusted to pH 7.4 with 0.5N sodium hydroxide. Next, 25 U of purine nucleoside phosphorylase was added. The reaction mixture was stirred at 25°–30° C. while maintaining the pH at 7.4. The progress of the reaction was monitored by HPLC. The reaction was terminated after approximately four days, when no further increase in product formation was observed by HPLC. At the end of the four day reaction period, the adenine was completely converted to adenosine. FIG. 1 provides a schematic for the process of Example 1.

EXAMPLE 2

To 10 ml of 0.1M phosphate buffer (pH 7) was added 1.0 mmol of the first nucleoside, 7-methylguanosine.hydroiodide, and 0.25 mmol of the unactivated heterocyclic base, 4-amino-1-H-imidazo[4,5-c]pyridine ("3-deazaadenine"). The solution was adjusted to pH 7.4 with 0.5N sodium hydroxide. Next, 250 U of purine nucleoside phosphorylase was added. The reaction mixture was stirred at 25°–30° C while maintaining the pH at 7.4. The progress of the reaction was monitored by HPLC. The reaction was terminated after approximately two days, when no further increase in product formation was observed by HPLC. At the end of the two day reaction period, 65% of the 3-deazaadenine was converted to 3-deazaadenosine. FIG. 2 provides a schematic for the process of Example 2.

EXAMPLE 3

To 10 ml of 0.1M phosphate buffer (pH 7) was added 1.0 mmol of the first nucleoside, 7-methylguanosine.hydroiodide, and 0.25 mmol of the unactivated heterocyclic base, 1,2,4-triazole-3-carboxamide ("TCA"). The solution was adjusted to pH 7.4 with 0.5N sodium hydroxide. Next, 100 U of purine nucleoside phosphorylase was added. The reaction mixture was stirred at 25°–30° C. while maintaining the pH at 7.4. The progress of the reaction was monitored by HPLC. The reaction was terminated after approximately two days, when no further increase in product formation was observed by HPLC. At the end of the two day reaction period, 54% of the TCA was converted to RTCA. FIG. 3 provides a schematic for the process of Example 3.

EXAMPLE 4

To 10 ml of 0.1M phosphate buffer (pH 7) was added 1.0 mmol of the first nucleoside, the neutralized zwitterionic form of 7-methylguanosine, and 0.25 mmol of the unactivated heterocyclic base, adenine. The solution was adjusted to pH 7.4 with 0.5N sodium hydroxide. Next, 25 U of purine nucleoside phosphorylase was added. The reaction mixture was stirred at 25°–30° C. while maintaining the pH at 7.4. The progress of the reaction was monitored by HPLC. The reaction was terminated after approximately four days, when no further increase in product formation was observed by HPLC. At the end of the four day reaction period, the adenine was completely converted to adenosine. FIG. 4 provides a schematic for the process of Example 4.

EXAMPLE 5

To 10 ml of 0.1M phosphate buffer (pH 7) was added 1.0 mmol of the first nucleoside, the neutralized zwitterionic form of 7-methylguanosine, and 0.25 mmol of the unactivated heterocyclic base, 3-deazaadenine. The solution was adjusted to pH 7.4 with 0.5N sodium hydroxide. Next, 250 U of purine nucleoside phosphorylase was added. The reaction mixture was stirred at 25°–30° C. while maintaining the pH at 7.4. The progress of the reaction was monitored by HPLC. The reaction was terminated after approximately two days, when no further increase in product formation was observed by HPLC. At the end of the two day reaction period, 70% of the 3-deazaadenine was converted to 3-deazaadenosine. The insoluble materials were removed by filtration. The products were recovered from the filtrate by lyophilization and chromatography. The product was characterized by its ultraviolet and mass spectrum. Observed: UV max pH 1, 260 nm; pH 13, 266 nm. Reported: UV max pH 1, 262 nm; pH 13, 265 nm. See Rousseau, et al. *Biochemistry*, 1966, Vol. 5, p. 756. Fast atom bombardment mass spectroscopy showed the molecular weight of the product to be 266. FIG. 5 provides a schematic for the process of Example 5.

EXAMPLE 6

To 10 ml of 0.1M phosphate buffer (pH 7) was added 1.0 mmol of the first nucleoside, the neutralized zwitterionic form of 7-methylguanosine, and 0.25 mmol of the unactivated heterocyclic base, TCA. The solution was adjusted to pH 7.4 with 0.5N sodium hydroxide. Next, 100 U of purine nucleoside phosphorylase was added. The reaction mixture was stirred at 25°–30° C. while maintaining the pH at 7.4. The progress of the reaction was monitored by HPLC. The reaction was terminated after approximately two days, when no further increase in product formation was observed by HPLC. At the end of the two day reaction period, 60% of the TCA was converted to RTCA. The insoluble materials were removed by centrifugation. The product was recovered by chromatography (see Utagawa, et al., *Agric. Biol. Chem.*, 1986, Vol. 50, pp. 121–126) and lyophilization.

The product appeared to be chromatographically identical to an authentic sample of RTCA obtained from Sigma Chemical Company, St. Louis, Mo. FIG. 6 provides a schematic for the process of Example 6.

EXAMPLE 7

To 10 ml of 0.1M phosphate buffer (pH 7) was added 1.0 mmol of the first nucleoside, the neutralized zwitterionic form of 7-methylinosine, and 0.25 mmol of the unactivated heterocyclic base, adenine. The solution was adjusted to pH 7.4 with 0.5N sodium hydroxide. Next, 25 U of purine nucleoside phosphorylase was added. The reaction mixture was stirred at 25°–30° C. while maintaining the pH at 7.4. The progress of the reaction was monitored by HPLC. The reaction was terminated after approximately two days, when no further increase in product formation was observed by HPLC. At the end of the two day reaction period, 90% of the adenine was converted to adenosine. FIG. 7 provides a schematic for the process of Example 7.

EXAMPLE 8

To 10 ml of 0.1M phosphate buffer (pH 7) was added 1.0 mmol of the first nucleoside, the neutralized zwitterionic form of 7-methylinosine, and 0.25 mmol of the unactivated heterocyclic base, 3-deazaadenine. The solution was adjusted to pH 7.4 with 0.5N sodium hydroxide. Next, 250 U of purine nucleoside phosphorylase was added. The reaction mixture was stirred at 25°–30° C. while maintaining the pH at 7.4. The progress of the reaction was monitored by HPLC. The reaction was terminated after approximately two days, when no further increase in product formation was observed by HPLC. At the end of the two day reaction period, 73% of the 3-deazaadenine was converted to 3-deazaadenosine. FIG. 8 provides a schematic for the process of Example 8.

EXAMPLE 9

To 10 ml of 0.1M phosphate buffer (pH 7) was added 1.0 mmol of the first nucleoside, the neutralized zwitterionic form of 7-methylinosine, and 0.25 mmol of the unactivated heterocyclic base, TCA. The solution was adjusted to pH 7.4 with 0.5N sodium hydroxide. Next, 100 U of purine nucleoside phosphorylase was added. The reaction mixture was stirred at 25°–30° C. while maintaining the pH at 7.4. The progress of the reaction was monitored by HPLC. The reaction was terminated after approximately two days, when no further increase in product formation was observed by HPLC. At the end of the two day reaction period, 57% of the TCA was converted to RTCA. FIG. 9 provides a schematic for the process of Example 9.

The general experimental procedure described in the above examples may be amenable to modification. For example, replacement of up to 50% of the aqueous solution volume with acetonitrile should be tolerated by the enzyme. In the presence of high concentrations of acetonitrile, the reaction yields should be unaffected, or in some cases slightly enhanced, particularly when 3-deazaadenosine is used as the first nucleoside. Other acceptable solvents will be apparent to those of ordinary skill in the art.

The neutralized zwitterionic form of 7-methylguanosine (the first nucleoside of examples 4–6) may provide a slight advantage over its hydroiodide salt (the first nucleoside of examples 1–3) both in ease of preparation and in yield of the second nucleoside, i.e., the transribosylation product.

As the yields of examples 7–9 show, transribosylation using 7-methylinosine (the first nucleoside of Examples 7–9) is effective in the process of the present invention. Two factors may favor the use of the methylated guanosines over the methylated inosine, however. First, the commercial cost of guanosine may be approximately half that of inosine. Second, 7-methylguanine appears to be very insoluble. During the transribosylation reactions of examples 1–6, the phosphorolysis of 7-methylguanosine produced 7-methylguanine which precipitated out of solution. Upon completion of the reaction, any residual donor molecules can be cleaved by mild acid hydrolysis and the solid 7-methylguanine nearly quantitatively removed by filtration or centrifugation.

Additional advantages and modifications will readily occur to those skilled in the art. The invention in its broader aspects is, therefore, not limited to the specific details and the illustrative examples as shown and described. Departures may be made from the detail without departing from the spirit or scope of the disclosed general inventive concept.

What is claimed is:

1. An essentially irreversible process for synthesizing nucleosides comprising:
   (a) reacting in an essentially irreversible manner, in solution and in the presence of a nucleoside-forming enzyme (i) a first nucleoside comprising a first modified heterocyclic base, that has been modified with a substituent selected from the group consisting of alkyl, alkylphenyl, hydroxy alkyl, and hydroxy alkylphenyl substituents, bonded to a glycosyl component with (ii) a second unmodified heterocyclic base, the first modified heterocyclic base, when dissociated from the glycosyl component of the first nucleoside, providing a relatively poor substrate for the nucleoside-forming enzyme as compared to the second unmodified heterocyclic base, for a time sufficient to enable the first nucleoside to donate the glycosyl component in an essentially irreversible manner for bonding with the second unmodified heterocyclic base;
   (b) yielding a mixture that includes (i) a second nucleoside comprising the second unmodified heterocyclic base bonded to the glycosyl component and (ii) the first modified heterocyclic base that has been dissociated from the glycosyl component, and
   (c) isolating the resulting second nucleoside from the mixture.

2. The process of claim 1 wherein the first nucleoside is selected from the group consisting of modified adenosine, guanosine, inosine, uridine, cytidine, thymidine, deoxyadenosine, deoxyguanosine, deoxyinosine, deoxythymidine, deoxyuridine, and deoxycytidine.

3. The process of claim 1 wherein the first nucleoside is a modified nucleoside-5-phosphate selected from the group consisting of modified adenosine-5-phosphate, guanosine-5-phosphate, inosine-5-phosphate, thymidine-5-phosphate, uridine-5-phosphate, cytidine-5-phosphate, deoxyadenosine-5-phosphate, deoxyguanosine-5-phosphate, deoxyinosine-5-phosphate, deoxythymidine-5-phosphate, deoxyuridine-5-phosphate, and deoxycytidine-5-phosphate.

4. The process of claim 1 wherein the nucleoside-forming enzyme is selected from the group consisting of purine nucleoside phosphorylase, pyrimidine nucleoside phosphorylase, uridine phosphorylase, thymidine phosphorylase, nucleoside ribosyltransferase, nucleoside deoxyribosyltransferase, adenine phosphoribosyltransferase, hypoxanthine phosphoribosyltransferase, uracil phosphoribosyltransferase, guanosine phosphorylase, and 5-methylthioadenosine phosphorylase.

5. An essentially irreversible process for synthesizing nucleosides comprising:
(a) reacting in an essentially irreversible manner, in solution and in the presence of a nucleoside-forming enzyme (i) an alkylated nucleoside comprising an alkylated heterocyclic base, that has been modified with an alkyl substituent, bonded to a glycosyl component with (ii) a heterocyclic base for a time sufficient to enable the alkylated nucleoside to donate the glycosyl component in an essentially irreversible manner for bonding with the heterocyclic base to yield a mixture that includes a nucleoside comprising the heterocyclic base bonded to the glycosyl component; and
(b) isolating the resulting nucleoside from the mixture.

6. The process of claim 5 wherein the glycosyl component of the alkylated nucleoside is selected from the group consisting of a ribose, a ribose analog, a ribose derivative, a deoxyribose, a deoxyribose analog, and a deoxyribose derivative.

7. The process of claim 6 wherein the glycosyl component is selected from the group consisting of a ribose, a ribose-5-phosphate, a deoxyribose, and a deoxyribose-5-phosphate.

8. The process of claim 7 wherein the alkylated heterocyclic base is selected from the group consisting of an alkylated purine, an alkylated purine analog, an alkylated purine derivative, an alkylated pyrimidine, an alkylated pyrimidine analog, and an alkylated pyrimidine derivative.

9. The process of claim 8 wherein the alkylated nucleoside is selected from the group consisting of a methylguanosine and a methylinosine.

10. The process of claim 5 wherein the heterocyclic base is selected from the group consisting of a purine, a purine analog, a purine derivative, a pyrimidine, a pyrimidine analog, and a pyrimidine derivative.

11. The process of claim 10 wherein the heterocyclic base is selected from the group consisting of adenine, deazaadenine and 1,2,4-triazole-3-carboxamide.

12. The process of claim 5 wherein the pH of the solution is maintained between about 6.8 and about 8.0.

13. An essentially irreversible process for synthesizing nucleosides comprising:
(a) reacting in an essentially irreversible manner, in solution and in the presence of a nucleoside phosphorylase enzyme and an effective amount of a phosphate (i) a first nucleoside comprising a first modified heterocyclic base, that has been modified with a substituent selected from the group consisting of alkyl, alkylphenyl, hydroxy alkyl, and hydroxy alkylphenyl substituents, bonded to a glycosyl component with (ii) a second unmodified heterocyclic base, the first modified heterocyclic base, when dissociated from the glycosyl component of the first nucleoside, providing a relatively poor substrate for the nucleoside-forming enzyme as compared to the second unmodified heterocyclic base, for a time sufficient to enable the first nucleoside to donate the glycosyl component in an essentially irreversible manner, for bonding with the second unmodified heterocyclic base;
(b) yielding a mixture that includes (i) a second nucleoside comprising the second unmodified heterocyclic base bonded to the glycosyl component and (ii) the first modified heterocyclic base that has been dissociated from the glycosyl component; and
(c) isolating the resulting second nucleoside from the mixture.

14. The process of claim 13 wherein the glycosyl component is selected from the group consisting of a ribose, a ribose analog, a ribose derivative, a deoxyribose, a deoxyribose analog, and a deoxyribose derivative.

15. The process of claim 14 wherein the first nucleoside comprises an alkylated heterocyclic base that has been modified with an alkyl substituent, selected from the group consisting of an alkylated purine, an alkylated purine analog, an alkylated purine derivative, an alkylated pyrimidine, an alkylated pyrimidine analog, and an alkylated pyrimidine derivative, bonded to a glycosyl component, selected from the group consisting of a ribose, a ribose-5-phosphate, a deoxyribose, and a deoxyribose-5-phosphate, and wherein the second unmodified heterocyclic base is selected from the group consisting of a purine, a purine analog, a purine derivative, a pyrimidine, a pyrimidine analog, and a pyrimidine derivative.

16. The process of claim 15 wherein the nucleoside phosphorylase enzyme is selected from then group consisting of a purine nucleoside phosphorylase and a pyrimidine nucleoside phosphorylase.

17. A process for synthesizing nucleosides comprising:
(a) reacting in solution and in the presence of a nucleoside phosphorylase enzyme and an effective amount of a phosphate (i) a first nucleoside, selected from the group consisting of a methylguanosine and a methylinosine, with (ii) a heterocyclic base, selected from the group consisting of adenine, deazaadenine, and 1,2,4-triazole-3-carboxamide, for a time sufficient to enable the first nucleoside to donate a ribose component for bonding with the heterocyclic base to yield a mixture that includes a second nucleoside comprising the heterocyclic base bonded to the ribose component; and
(b) isolating the resulting second nucleoside from the mixture.

18. The process of claim 17 wherein the nucleoside phosphorylase enzyme is purine nucleoside phosphorylase.

19. The process of claim 18 wherein the first nucleoside is selected from the group consisting of a 7-methylguanosine and a 7-methylinosine.

* * * * *